United States Patent [19]

Frankel et al.

[11] Patent Number: 4,683,085
[45] Date of Patent: Jul. 28, 1987

[54] POLYAZIDO ESTERS

[75] Inventors: Milton B. Frankel, Tarzana; Edgar R. Wilson, Simi Valley, both of Calif.

[73] Assignee: Rockwell International Corporation, El Segundo, Calif.

[21] Appl. No.: 766,459

[22] Filed: Aug. 19, 1985

[51] Int. Cl.$^4$ .............................................. C07C 117/00
[52] U.S. Cl. .................... 260/349; 149/19.1; 149/19.5; 149/88
[58] Field of Search ........................................ 260/349

[56] References Cited

U.S. PATENT DOCUMENTS

| | | | |
|---|---|---|---|
| 4,141,910 | 2/1979 | Flanagan et al. | 260/349 |
| 4,406,718 | 9/1983 | Frankel et al. | 260/349 X |
| 4,432,814 | 2/1984 | Witucki et al. | 149/19.1 |
| 4,472,311 | 9/1984 | Frankel et al. | 260/349 |

OTHER PUBLICATIONS

Royals; Advanced Organic Chemistry, (1954), p. 605; Constable & Co. Ltd., London.
Hilgetag, et al; Preparative Organic Chemistry, (1972), p. 378, John Wiley & Sons, N.Y.

Primary Examiner—Joseph Paul Brust
Attorney, Agent, or Firm—H. Fredrick Hamann; Harry B. Field; David C. Faulkner

[57] ABSTRACT

Energetic plasticizers comprising 4,4,4-trinitrobutyryl and 1,3,5-benzene tricarboxylic acid esters of pentaerythritol triazide and pentaerythritol diazido mononitrate, prepared by reacting the appropriate acid chloride, e.g. 4,4,4-trinitrobutyryl chloride, with pentaerythritol triazide or pentaerythritol diazido mononitrate.

2 Claims, No Drawings

POLYAZIDO ESTERS

BACKGROUND OF THE INVENTION

1. Field of the Invention

This invention relates to production of new azido compounds, and is particularly directed to the preparation of polyazido esters derived from pentaerythritol polyazides, together with a method for producing such compounds.

2. Description of the Prior Art

Solid propellants are formulated from an oxidizer and fuel together with suitable binders and plasticizers to impart physical integrity. Most highly energetic systems utilize binders and plasticizers containing energetic groups such as nitro ($-NO_2$), fluorodinitro ($FC(NO_2)_2-$), difluoroamino ($-NF_2$), and many others.

Utilization of azido plasticizers has become a reality during the last several years. These azido plasticizers impart additional energy to propellants since each azido group present adds approximately 85 kcal/mole of energy to the system.

SUMMARY OF THE INVENTION

Accordingly, there is provided by the present invention energetic plasticizers having the general formula:

$$RCOO-CH_2-\underset{\underset{CH_2N_3}{|}}{\overset{\overset{CH_2N_3}{|}}{C}}CH_2X$$

where R is 4,4,4-trinitrobutyryl or the 1,3,5-benzene tricarboxylic acid acyl group, and X is $-N_3$ or $-ONO_2$.

Such compounds are prepared by reacting the appropriate acid chloride, that is RCOCl where R and have the values noted above, with pentaerythritol triazide or pentaerythritol diazido mononitrate.

OBJECTS OF THE INVENTION

It is therefore an object of the present invention to provide improved materials for formulating solid propellants.

Another object of the present invention is the provision of new compositions of matter.

Another object of the present invention is to provide energetic azido compounds in the form of polyazido esters.

A specific object of the present invention is to provide certain esters of pentaerythritol triazide and pentaerythritol diazido mononitrate.

DESCRIPTION OF THE PREFERRED EMBODIMENTS

In accordance with the present invention there are provided esters of certain acid chlorides with pentaerythritol triazide or pentaerythritol diazido mononitrate, according to the following reaction:

$$RCOCl + HOCH_2-\underset{\underset{CH_2N_3}{|}}{\overset{\overset{CH_2N_3}{|}}{C}}CH_2X \longrightarrow RCOO-CH_2-\underset{\underset{CH_2N_3}{|}}{\overset{\overset{CH_2N_3}{|}}{C}}CH_2X$$

where R is 4,4,4-trinitrobutyryl or the 1,3,5-benzene tricarboxylic acid acyl group, and X is $-N_3$ or $-ONO_2$.

The acid chlorides employed in the above reaction are 4,4,4-trinitrobutyryl chloride and 1,3,5-benzene tricarboxylic acid chloride. These are known, commercially available compounds.

The pentaerythritol compounds which are reacted with the acid chlorides contain a free functional hydroxy group and two or three azide groups. The specific pentaerythritol intermediates in the reaction are pentaerythritol triazide and pentaerythritol diazido mononitrate. These pentaerythritol intermediates and their method of preparation are disclosed in the copending application Ser. No. 766,460, filed Aug. 19, 1985, titled "Azido Derivatives of Pentaerythritol", by the same inventors as the present application and assigned to the same assignee as the present application.

Thus, for example pentaerythritol triazide is prepared by the reaction of 3,3-bis(azidomethyl) oxetane with hydrobromic acid to produce pentaerythritol diazido monobromide, followed by reaction thereof with sodium azide, and pentaerythritol diazido mononitrate is prepared by reaction of 3,3-bis(azidomethyl) oxetane with nitric acid.

The disclosure of the above application Ser. No. 766,460 is incorporated herein by reference.

Examples of the azido esters according to the present invention are as follows:

$$(NO_2)_3CCH_2CH_2CO_2CH_2C(CH_2N_3)_3 \qquad (1)$$

$$(NO_2)_3CCH_2CH_2CO_2CH_2\underset{\underset{CH_2N_3}{|}}{\overset{\overset{CH_2N_3}{|}}{C}}CH_2ONO_2 \qquad (2)$$

$$(N_3CH_2)_3CCH_2O_2C-\text{benzene}-CO_2CH_2C(CH_2N_3)_3 \qquad (3)$$

with a third $CO_2CH_2C(CH_2N_3)_3$ substituent on the ring.

It will be noted that the above compounds (1) (2) and (3) of the invention have a multiplicity of azido groups, or a multiplicity of azido and nitro groups, and such polyazido and polyzaido/polynitro substituted esters are highly effective as energetic plasticizers, which particularly function to increase the burn rate of minimum smoke solid propellants.

Thus, for example, compound (1) above is prepared by the following reaction:

$$(NO_2)_3CCH_2CH_2COCl + HOCH_2C(CH_2N_3)_3 \rightarrow (NO_2)_3CCH_2CH_2CO_2CH_2C(CH_2N_3)_3$$

The reaction between the acid chloride, e.g. 4,4,4-trinotrobutyryl chloride, and the pentaerythritol azide, e.g. pentaerythritol triazide, is carried out, generally employing an excess of the acid chloride over the pentaerythritol azide intermediate, in an appropriate organic solvent such as a halogenated solvent, particularly a chlorinated solvent such as methylene chloride, ethylene dichloride, carbon tetrachloride or chloroform. The preferred halogenated solvents are methylene chloride and ethylene dichloride. In some instances an HCl acceptor such as pyridine can be employed.

The reaction can be conveniently carried out at reflux temperatures, or at lower temperatures, e.g. 15°–25° C., particularly when employing an HCl acceptor.

After completion of the reaction to produce the azido ester product, the reaction mixture is treated with sodium bicarbonate solution and the organic phase is separated. The organic phase is then washed with water, dried, e.g. over magnesium sulfate, and passed through a column of neutral alumina or silica gel, for purification. The halogenated solvent solution of the azido ester product can be concentrated by distillation to remove the solvent and obtain the azido ester product, in the form of an oil, which can be further purified, if desired. The azido ester product can be used as an energetic plasticizer in the formulation of solid propellants.

The following are examples of practice of the invention, but it will be understood that such examples are only illustrative and not limitative of the invention.

EXAMPLE I tris(2,2,2-azidomethyl) ethyl 4,4,4-Trinitrobutyrate—Compound (1)

A solution of 3.81 g (0.016 m) of 4,4,4-trinitrobutyryl chloride, 3.06 g (0.014 m) of pentaerythritol triazide, and 10 ml of ethylene dichloride was refluxed for 70 hours. At this time, G.C. analysis showed no starting materials. The reaction mixture was diluted with 20 ml of methylene chloride and stirred with 20 ml of dilute sodium bicarbonate solution for one hour at ambient temperature.

The organic phase was separated, washed with water, dried over magnesium sulfate, passed through a column of neutral alumina, and concentrated to give 5.35 g (91.9%) of yellow oil, $n^{21}D$ 1.5194. The infrared spectrum was consistent with the expected structure of the ester product, with strong absorption at $4.8\mu$ ($N_3$), $5.8\mu$ (C=O), and $6.35\mu$ ($NO_2$). Liquid chromatography (LC) analysis showed only a single component.

The above prepared trisazido ester has a positive heat of formation of +96 Kcal/mole, and can be employed as an energetic plasticizer for increasing the burn rate of minimum smoke solid propellants.

EXAMPLE II

3-Nitrato-2,2-bis(azidomethyl1) propyl 4,4,4-Trinitrobutyrate—Compound (2)

A solution of 22.3 g (0.092 m) of 4,4,4-trinitrobutyryl chloride, 19.4 g (0.084 m) of pentaerythritol diazido mononitrate and 65 ml of ethylene dichloride was refluxed for 90 hours. The cooled reaction mixture was washed with water and dilute sodium bicarbonate solution. The organic phase was separated, washed with water, dried over magnesium sulfate, and concentrated to yield 34.6 g (94.5%) light yellow oil, $n^{26}D$ 1.5105. The product was dissolved in 105 ml of methylene chloride and passed through a column of silica gel. Concentration of the solution gave 31.7 g (86.6%) of pale yellow liquid, $n^{26}D$ 1.5108. The infrared spectrum was consistent with the expected structure of the ester product. Purity by LC analyses was 99+%.

EXAMPLE III 1,3,5-tris(2,2,2-Azidomethyl) ethyl Benzene Tricarboxylate—Compound (3)

To a solution of 5.31 g (0.02 m) of 1,3,5-benzene tricarboxylic acid chloride, 13.07 g (0.062 m) of pentaerythritol triazide, and 30 ml of ethylene dichloride was added dropwise 4.9 g (0.062 m) of pyridine. The reaction temperature was maintained at 15° to 25° C. by external cooling with an ice-bath. After the addition was complete the reaction mixture was stirred overnight at ambient temperature, then washed with water and dilute sodium bicarbonate. The organic phase was separated, washed with water, dried over anhydrous sodium sulfate, and passed through a silica gel column. Concentration of the solution gave 12.3 g (77.9%) of crude oil. Purification from a chloroform-methanol solution gave crystals, m.p. 65°–68° C.

From the foregoing, it is seen that the invention provides a series of new compounds in the form of esters of pentaerythritol azides, containing a plurality of azide groups, and which can also contain a plurality of nitro groups, providing a class of energetic plasticizers for use in the formulation of solid propellants, and a method for preparation of such compounds.

It is to be understood that what has been described is merely illustrative of the principles of the invention and that numerous arrangements in accordance with this invention may be devised by one skilled in the art without departing from the spirit and scope thereof.

What is claimed is:

1. A polyazido monoester having the general formula:

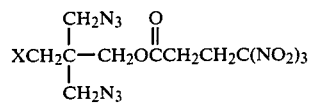

wherein X is $N_3$ or $ONO_2$.

2. A polyazido triester having the formula:

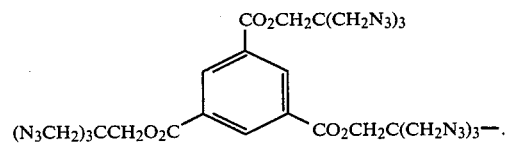

* * * * *